United States Patent
Pérez Simón et al.

(10) Patent No.: US 10,045,994 B2
(45) Date of Patent: Aug. 14, 2018

(54) AGENTS FOR TREATING MULTIPLE MYELOMA

(71) Applicant: SERVICIO ANDALUZ DE SALUD, Sevilla (ES)

(72) Inventors: José Antonio Pérez Simón, Sevilla (ES); María Victoria Barbado González, Sevilla (ES)

(73) Assignee: SERVICIO ANDALUZ DE SALUD, Sevilla (ES)

( * ) Notice: Subject to any disclaimer, the term of this patent is extended or adjusted under 35 U.S.C. 154(b) by 0 days.

(21) Appl. No.: 14/897,333

(22) PCT Filed: Jun. 13, 2014

(86) PCT No.: PCT/ES2014/070491
§ 371 (c)(1),
(2) Date: Dec. 10, 2015

(87) PCT Pub. No.: WO2014/198993
PCT Pub. Date: Dec. 18, 2014

(65) Prior Publication Data
US 2016/0120874 A1 May 5, 2016

(30) Foreign Application Priority Data
Jun. 13, 2013 (ES) .................................. P201330884

(51) Int. Cl.
| | |
|---|---|
| *A01N 37/36* | (2006.01) |
| *A61K 31/60* | (2006.01) |
| *A61K 31/5383* | (2006.01) |
| *A61K 31/198* | (2006.01) |
| *A61K 31/395* | (2006.01) |
| *A61K 31/454* | (2006.01) |
| *A61K 31/573* | (2006.01) |
| *A61K 31/69* | (2006.01) |
| *A61K 31/704* | (2006.01) |
| *A61K 38/07* | (2006.01) |
| *A61K 45/06* | (2006.01) |

(52) U.S. Cl.
CPC ........ *A61K 31/5383* (2013.01); *A61K 31/198* (2013.01); *A61K 31/395* (2013.01); *A61K 31/454* (2013.01); *A61K 31/573* (2013.01); *A61K 31/69* (2013.01); *A61K 31/704* (2013.01); *A61K 38/07* (2013.01); *A61K 45/06* (2013.01)

(58) Field of Classification Search
USPC .......................................................... 514/160
See application file for complete search history.

(56) References Cited

U.S. PATENT DOCUMENTS

2013/0172388 A1* 7/2013 Xie .................. C07C 311/18
514/331

FOREIGN PATENT DOCUMENTS

EP 2719375 A1 4/2014

OTHER PUBLICATIONS

Casarejos, M.J. et al., "Natural cannabinoids improve dopamine neurotransmission and tau and amyloid pathology in a mouse model of tauopathy," *Journal of Alzheimer's Disease*, vol. 35, pp. 525-539, 2013.
Gallily, R. et al., "γ-Irradiation enhances apoptosis induced by cannabidiol, a non-psychotropic cannabinoid, in cultured Hl-60 myeloblastic leukemia cells," *Leukemia & Lymphoma*, vol. 44, No. 10, pp. 1767-1773, 2003.
International Search Report for PCT/ES2014/070491, dated Sep. 19, 2014.
McKallip, R.J. et al., "Cannabidiol-induced apoptosis in human leukemia cells: a novel role of cannabidiol in the regulation of $p22^{phox}$ and Nox4 expression," *Molecular Pharmacology*, vol. 70, No. 3, pp. 897-908, 2006.
McKallip, R.J. et al., "Targeting CB2 cannabinoid receptors as a novel therapy to treat malignant lymphoblastic disease," *Blood*, vol. 100, No. 2, pp. 627-634, 2002.
Morelli, M. B. et al., "The effects of cannabidiol and its synergism with bortezomib in multiple myeloma cell lines. A role for transient receptor potential vanilloid type-2," *International Journal of Cancer*, vol. 134, pp. 2534-2546, 2014.
Powles, et al. "Cannabis-induced cytotoxicity in leukemic cell lines: the role of the cannabinoid receptors and the MAPK pathway," *Blood*, vol. 105, No. 3, pp. 1214-1221, 2005.

* cited by examiner

*Primary Examiner* — Marcos L Sznaidman
(74) *Attorney, Agent, or Firm* — McCarter & English, LLP; Jill Ann Mello

(57) ABSTRACT

The present invention relates to the use of compounds of a cannabinoid nature for inhibiting viability with increasing doses of myeloma cell lines. Furthermore, said compounds have been shown not to affect CD34+ cells (normal hematopoietic progenitors) in terms of viability and proliferation. For this reason, the invention paves the way for the use of compounds of a cannabinoid nature as a promising therapy against multiple myeloma and related diseases.

7 Claims, 5 Drawing Sheets

AGENTS FOR TREATING MULTIPLE MYELOMA

RELATED APPLICATIONS

This application is a 35 U.S.C. § 371 national stage filing of International Application No. PCT/ES2014/070491, filed on Jun. 13, 2014, which claims priority to Spanish Patent Application No. P201330884, filed on Jun. 13, 2013. The entire contents of each of the foregoing applications are incorporated herein by reference.

FIELD OF THE INVENTION

The present invention is comprised in the field of medicine and the pharmacy and relates to the use of cannabinoid agents for preparing a medicinal product for the treatment of monoclonal gammopathies in general, and for the treatment of multiple myeloma in particular.

BACKGROUND OF THE INVENTION

Multiple myeloma (MM) is a malignant hemopathy characterized by clonal proliferation of plasma cells.

The incidence rate of MM is of 4-5 out of 100,000 inhabitants and year. The age of onset is around the 65 years, and although the therapeutic arsenal has been expanded in recent years with the development of new molecules, such as proteosome inhibitors or immunomodulatory drugs (IMIDs), which have been added to conventional treatments such as melfalan and prednisone, in addition to the hematopoietic progenitor cell transplant, MM is still considered an incurable disease.

Therefore, with the treatments available up until now, a five-year survival rate for MM is still low, especially when compared with other types of cancer. For this reason, there is a need to provide alternative treatments with respect to current treatments.

BRIEF DESCRIPTION OF THE INVENTION

A first aspect of the invention relates to the use of a cannabinoid agent in the preparation of a medicinal product for the prevention and/or treatment of a monoclonal gammopathy. In a preferred embodiment, the monoclonal gammopathy is selected from the list consisting of multiple myeloma, plasma cell leukemia, Waldenström macroglobulinemia and amyloidosis. In an even more preferred embodiment, the monoclonal gammopathy is multiple myeloma.

In another preferred embodiment of the first aspect of the invention, the cannabinoid agent is selected from natural cannabinoid agents or synthetic cannabinoid agents. In another preferred embodiment, the synthetic cannabinoid agent is selected from a CB1 receptor agonist, a CB2 receptor agonist, or a mixed agonist.

In another more preferred embodiment, the synthetic cannabinoid agent is selected from the list consisting of: HU-308; JWH-133; L-759, 633; PRS 211,375; AM-1241; JWH-015; L-759, 656; GW-842, 166X; GP-1a; THC (tetrahydrocannabinol); HU-210; L-759, 656; WIN 55,212-2; CP 55940; CRA-13; SAB-378; JWH-018 (AM-678); CP 50,556-1 (levonantradol); cannabidiol+THC, or any combinations thereof.

More preferably, the cannabinoid agent is WIN 55,212-2.

In another preferred embodiment of the first aspect of the invention, the cannabinoid agent is natural and is selected from the list consisting of: cannabigerol (CBG) type agents, cannabichromene (CBC) type agents, cannabidiol (CBD) type agents, cannabinodiol (CBND) type agents, tetrahydrocannabinol (THC) type agents, cannabinol (CBN) type agents, cannabitriol (CBT) agents, cannabielsoin (CBE) agents, isocannabinoid agents, cannabicyclol (CBL) type agents, cannabicitran (CBT) type agents, cannabichromanone (CBCN) type agents, or any combinations thereof.

Therefore, in another preferred embodiment of the first aspect of the invention the natural cannabinoid agent is a cannabigerol (CBG) type agent, which is selected from the list consisting of: cannabigerol (E)-CBG-$C_5$; cannabigerol monomethyl ether (E)-CBGM-$C_5$A; cannabinerolic acid A (2)-CBGA-$C_5$A; cannabigerovarin (E)-CBGV-$C_3$; cannabigerolic acid A (E)-CBGA-$C_5$A; cannabigerolic acid A monomethyl ether (E)-CBGAM-$C_5$A; cannabigerovarinic acid A (E)-CBGVA-$C_3$A, or any combinations thereof.

In another preferred embodiment of the first aspect of the invention, the natural cannabinoid agent is a cannabichromene (CBC) type agent, which is selected from the list consisting of: (±)-cannabichromene CBC-$C_5$; (±)-cannabichromenic acid A CBCA-$C_5$A; (±)-cannabichromevarin CBCV-$C_3$; (±)-cannabichromevarinic acid A CBCVA-$C_3$A, or any combinations thereof.

In another preferred embodiment, the natural cannabinoid agent is a cannabidiol (CBD) type agent, which is selected from the list consisting of: (−)-cannabidiol CBD-$C_5$; cannabidiol monomethyl ether CBDM-$C_5$; cannabidiol-$C_4$CBD-$C_4$; (−)-cannabidivarin CBDV-$C_3$; cannabidiorcol CBD-$C_1$; cannabidiolic acid CBDA-$C_5$; cannabidivarinic acid CBDVA-$C_3$, or any combinations thereof.

In another preferred embodiment, the natural cannabinoid agent is a cannabinodiol (CBND) type agent, which is selected from the list consisting of: cannabinodiol CBND-$C_5$; cannabinodivarin CBND-$C_3$, or any combinations thereof.

In another preferred embodiment, the natural cannabinoid agent is a tetrahydrocannabinol (THC) type agent, which is selected from the list consisting of: $\Delta^9$-Tetrahydrocannabinol $\Delta^9$-THC-$C_5$; $\Delta^9$Tetrahydrocannabinol-$C_4\Delta^9$-THC-$C_4$; $\Delta^9$-Tetrahydrocannabivarin $\Delta^9$-THCV-$C_3$; $\Delta^9$-Tetrahydrocannabiorcol $\Delta^9$-THCO-$C_1$; $\Delta^9$-Tetrahydrocannabinolic acid A $\Delta^9$-THCA-$C_5$ A; A $\Delta^9$-tetrahydrocannabinolic acid B $\Delta^9$-THCA-$C_5$B; $\Delta^9$-tetrahydrocannabinolic acid-$C_4$ A and/or B $\Delta^9$-THCA-$C_4$ A and/or B; $\Delta^9$-tetrahydrocannabivarinic acid A $\Delta^9$-THCVA-$C_3$ A; $\Delta$-tetrahydrocannabiorcolic acid A and/or B $\Delta^9$-THCOA-C A and/or B; (−)-$^8$-trans (6aR,10aR)-$\Delta^8$-Tetrahydrocannabinol $\Delta^8$-THC-$C_5$; (−)-$A^8$-trans-(6aR,10aR)-tetrahydrocannabinolic acid A $\Delta^8$-THCA-$C_5$ A; (−)-(6aS,10aR)-$\Delta^9$-tetrahydrocannabinol (−)-cis-$\Delta^9$-THC-$C_5$, or any combinations thereof.

In another preferred embodiment, the natural cannabinoid agent is an agent of the cannabinol (CBN) type, which is selected from the list consisting of: cannabinol CBN-$C_5$; cannabinol-C CBN-$C_4$; cannabivarin CBN-$C_3$; cannabinol-C2 CBN-$C_2$; cannabiorcol CBN-$C_1$; cannabinolic acid A CBNA-$C_5$ A; cannabinol methyl ether CBNM-$C_5$, or any combinations thereof.

In another preferred embodiment, the natural cannabinoid agent is a cannabitriol (CBT) type agent, which is selected from the list consisting of: (−)-(9R,10R)-trans-cannabitriol (−)-trans-CBT-$C_5$; (+)(9S,10S)-Cannabitriol (+)-trans-CBT-$C_5$; (±)-(9R,10S/9S,10R)-Cannabitriol (±)-cis-CBT-$C_5$; (−)-(9R,10R)-trans-10-O-Ethyl-cannabitriol (−)-trans-CBT-CEt-$C_5$; (±)-(9R,10R/9S,10S)-Cannabitriol-$C_3$ (±)-trans-CBT-$C_3$; 8,9-Dihydroxy-$\Delta^{6a(10a)}$-tetrahydrocannabinol 8,9-Di-OH-CBT-$C_5$; cannabidiolic acid A cannabitriol ester CBDA-$C_5$9-OH-CBT-$C_5$ ester; (−)-(6aR,9S,10S,10aR)-9, 10-Dihydroxy-hexahydrocannabinol, Cannabiripsol Cannabiripsol-$C_5$; (−)-6a,7,10$^a$Trihydroxy-$\Delta^9$-tetrahydrocannabinol (−)-Cannabitetrol; 10-Oxo-$\Delta^{6a(10a)}$ tetrahydrocannabinol OTHC, or any combinations thereof.

In another preferred embodiment, the natural cannabinoid agent is an agent of the cannabielsoin (CBE) type, which is selected from the list consisting of: (5aS,6S,9R,9aR)-Cannabielsoin CBE-$C_5$; (5aS,6S,9R,9aR)-$C_3$-Cannabielsoin CBE-$C_3$; (5aS,6S,9R,9aR)-cannabielsoic acid A CBEA-$C_5$ A; (5aS,6S,9R,9aR)-cannabielsoic acid B CBEA-$C_5$ B; (5aS,6S,9R,9aR)-$C_3$-cannabielsoic acid B CBEA-$C_3$ B; Cannabiglendol-$C_3$OH-iso-HHCV-$C_3$; Dehydrocannabifuran DCBF-$C_5$; Cannabifuran CBF-$C_5$, or any combinations thereof.

In another preferred embodiment, the natural cannabinoid agent is an agent of the isocannabinoid type, which is selected from the list consisting of: (−)-$\Delta_7$-trans-(1R,3R,6R)-Isotetrahidrocannabinol; (±)-$\Delta^7$-1,2-cis-(1R,3R,6S/1S,3S,6R)-Isotetrahidrocannabivarin; (−)-$\Delta^7$-trans (1R,3R,6R)-Isotetrahidrocannabivarin, or any combinations thereof.

In another preferred embodiment, the natural cannabinoid agent is an agent of the cannabicyclol (CBL) type, which is selected from the list consisting of: (±)-(1 aS,3aR,8bR,8cR)-Cannabicyclol CBL-$C_5$; (±)-(1aS,3aR,8bR,8cR)-cannabicyclolic acid A CBLA-$C_5$ A; (±)-(1aS,3aR,8bR,8cR)-Cannabicyclovarin CBLV-$C_3$, or any combinations thereof.

In another preferred embodiment, the natural cannabinoid agent is an agent of the Cannabicitran (CBL) type, which is selected from the list consisting of: Cannabicitran CBT-$C_5$, or any combinations thereof.

In another more preferred embodiment, the natural cannabinoid agent is an agent of the Cannabichromanone (CBCN) type, which is selected from: Cannabichromanone CBCN-$C_5$; Cannabichromanone-C3; CBCN-$C_3$; Cannabicoumaronone CBCON-C5, or any combinations thereof.

A second aspect of the present invention relates to the use of a pharmaceutical composition comprising one of the cannabinoid agents described in the present invention for preparing a medicinal product for the prevention and/or treatment of a monoclonal gammopathy. More preferably, the monoclonal gammopathy is selected from the list consisting of: multiple myeloma, plasma cell leukemia, Waldenström macroglobulinemia and amyloidosis. In an even more preferred embodiment, the monoclonal gammopathy is multiple myeloma.

More preferably, the composition of the second aspect of the invention furthermore comprises another active ingredient. Even more preferably the active ingredient is selected from the list consisting of: Velcade, Melfalan, Prednisone, Revlimd, Dextamethasone, Thalidomide, Doxyrubicin, Bortezomid, Mozobil, granulocyte colony-stimulating factor, pomailidomide, carfizomid, or any combinations thereof. Even more preferably, the pharmaceutical composition comprises a pharmaceutically acceptable carrier.

Another aspect of the invention relates to the use of a combined preparation comprising a cannabioid agent of the invention and another active ingredient in the preparation of a medicinal product for the simultaneous or sequential combined administration thereof for the treatment of a monoclonal gammopathy. More preferably, the monoclonal gammopathy is selected from multiple myeloma, plasma cell leukemia, Waldenström macroglobulinemia, amyloidosis, or any combinations thereof. In an even more preferred embodiment, the monoclonal gammopathy is multiple myeloma. Even more preferably, the active ingredient is selected from Velcade, Melfalan, Prednisone, Revlimd, Dextamethasone, Thalidomide, Doxyrubicin, Bortezomid, Mozobil, granulocyte colony-stimulating factor, pomailidomide, carfizomid, or any combinations thereof.

In another preferred embodiment, the combined preparation of the invention furthermore comprises a pharmaceutically acceptable carrier. In another preferred embodiment, the combined preparation of the invention furthermore comprises another active ingredient.

DETAILED DESCRIPTION OF THE INVENTION

Multiple myeloma (MM) is a neoplasia characterized by the clonal proliferation of malignant plasma cells in the bone marrow and is associated with the presence of a monoclonal component or protein M in blood and/or serum.

For the purpose of obtaining an effective therapy against this disease, the authors of the present invention have surprisingly found that compounds of a cannabinoid nature are capable of inhibiting viability with increasing doses of myeloma cell lines, whereas CD34+ cells (normal hematopoietic progenitors), granulocytes and lymphocytes are not affected in terms of viability and proliferation. Therefore, this invention paves the way for the use of compounds of a cannabinoid nature as a promising therapy against multiple myeloma and related diseases.

In order to carry out the present finding, the authors of the present invention assessed whether the cannabinoid compound called WIN 55,212-2 with the following chemical formula (R)-(+)-[2,3-Dihydro-5-methyl-3-(4-morpholinyl-methyl)pyrrolo[1,2,3-de]-1,4 benzoxazin-6-yl]-1-naphtalenylmethanone, CAS number 131543-23-2, and structure (I):

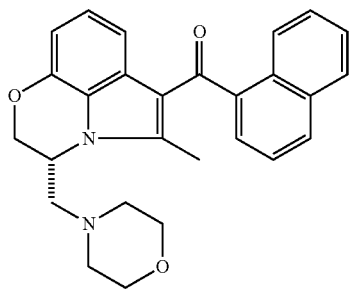

Structure (I)

was capable of inhibiting the viability of established myeloma cell lines, such as the myeloma cell line U266 and the multiple myeloma cell line MM1.S. It is observed that compound WIN 55,212-2 is a non-specific agonist of the CB1 and CB2 cannabinoid receptors.

In order to determine the effect of the cannabinoid compound WIN 55,212-2, myeloma cell line U266 was incubated for a period of 48 and 96 hours with increasing concentrations of WIN 55,212-2 between 0.5 and 50 uM; cell viability was determined by means of the MTT metabolization. The MTT assay is based on the capacity of the mitochondrial enzyme, succinate dehydrogenase, of viable cells for transforming the tetrazolium salt MTT into a blue-colored product, MTT formazan, which is proportional to the number of living cells present. The mean proliferation values of the untreated control cell cultures were taken as 100%.

Figure 1:
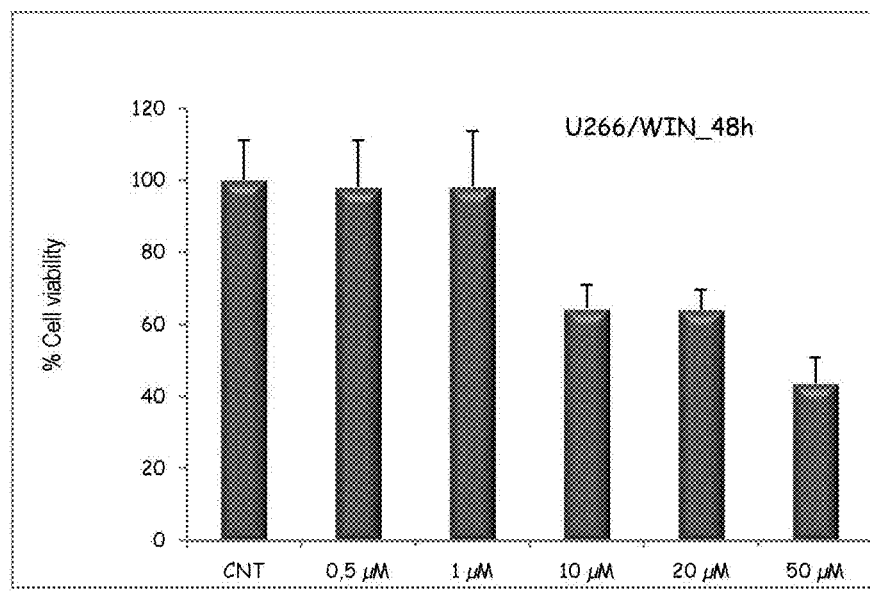
FIG. 1: Myeloma cell line U266 was incubated at the indicated concentrations with the cannabinoid WIN 55-212,2 for 48 h, and cell viability was determined by means of MTT metabolization. The mean proliferation values of the untreated control cell cultures were taken as 100%. The data corresponds to the means+/−the standard deviation of the triplicates of each of the 4 assays performed. U266 cell viability significantly drops ($p<0.05$) to concentrations of 10 uM and 20 uM to 40%, whereas cell viability inhibition reaches 60% at concentrations of 50 uM.

As can be seen in FIG. 1, concentrations between 10 uM and 20 uM of the compound WIN 55,212-2 were capable of inhibiting cell viability by about 40%, and concentrations of 50 uM produced an inhibition of cell viability of about 60%. Additionally, as seen in FIG. 2, longer incubation periods, specifically 96 hours, produced cell viability inhibition of about 80% at concentrations of 50 uM.

These same assays were repeated incubating the myeloma cell line U266 for a period of 48 hours with increasing concentrations of WIN 55,212-2 between 0.5 and 50 uM. Nevertheless, cell viability was determined by means of flow cytometry instead of by means of MTT metabolization; the results are illustrated in FIG. 3 and as can be seen, said results are very similar to those described above in FIGS. 1 and 2.

Figure 2:
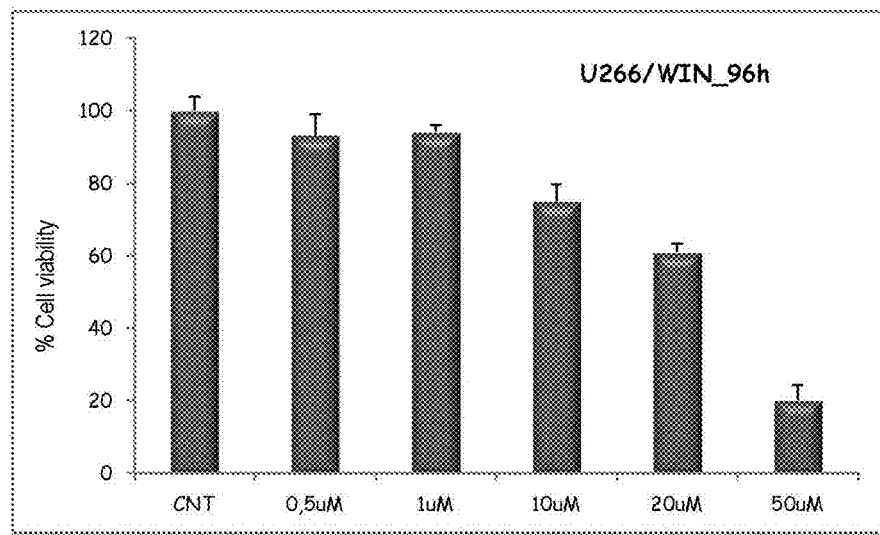
FIG. 2: This figure develops the data exemplified in FIG. 1 and shows how at longer times longer incubation times, 96 h, the drop in cell viability reaches 80% at concentrations of 50 uM.
Figure 3:
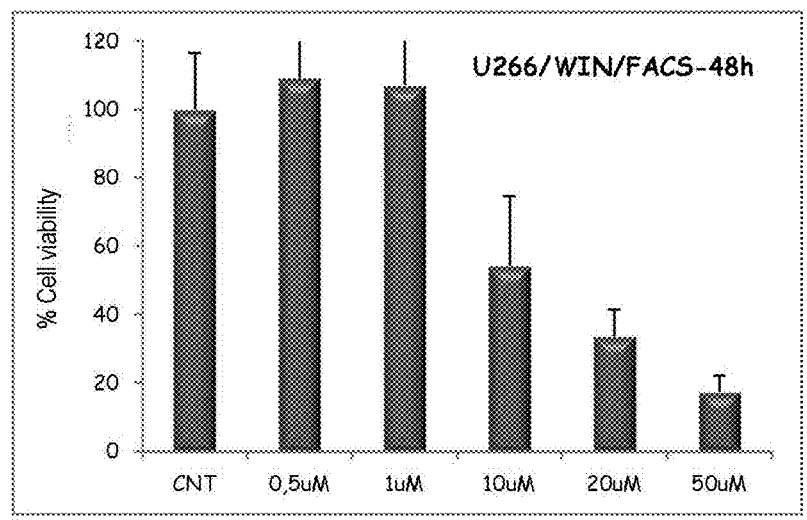
FIG. 3: The cell viability of line U266 after treatment for 48 h with the cannabinoid agent was also determined by flow cytometry by means of labeling with 7AAD. The results obtained were similar to those detected with the MTT assay. As seen in the figure, the cannabinoid has a cytotoxic effect on cells from concentrations of 10 uM, and this drop in cell viability is significant ($p<0.05$) according to the Student's t statistical analysis.

Therefore, due to the results described in FIGS. 1 to 3, it can clearly be determined how the cell viability of established myeloma cell lines drops significantly (p<0.05) at concentrations greater than 10 uM both at 48 hours and at longer incubation times.

For the purpose of verifying the preceding data, the authors of the present invention analyzed the capacity of the compound WIN 55,212-2 to inhibit viability of a second myeloma cell line, in this case multiple myeloma cell line MM1.S. The results of these experiments have been faithfully reflected in FIGS. 4 and 5.

Figure 4:
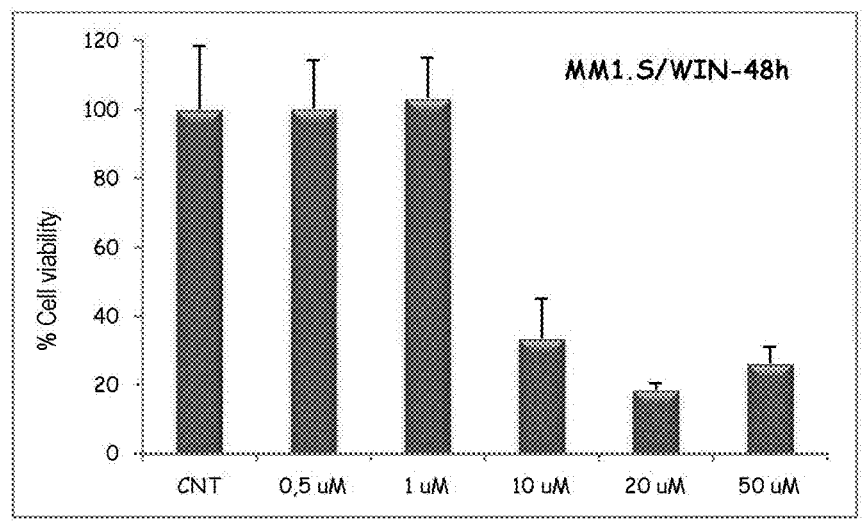
FIG. 4: The myeloma cell line MM1.S was incubated at increasing concentrations with the cannabinoid WIN 55-212,2 and cell viability was determined by means of the MTT metabolization. The mean proliferation values of the untreated control cell cultures were taken as 100%. The data corresponds to the means+/−the standard deviation of the triplicates of each of the 4 assays performed. At incubation times of 48 h, the cell viability of line MM1.S noticeably dropped after concentrations of 10 uM, 20 uM and 50 uM, with a cytotoxicity greater than 50%.
Figure 5:
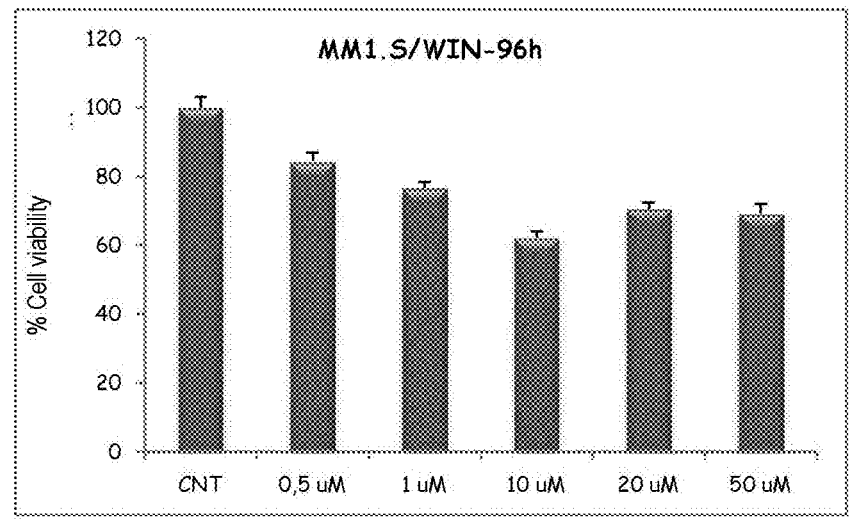
FIG. 5: This figure develops the data exemplified in FIG. 4 and shows that when the cell line is treated with the cannabinoid for longer incubation times (96 h), cell viability is also affected at the same doses of WIN 55-212,2; nevertheless this drop is lower than at short incubation times.
Figure 6A:
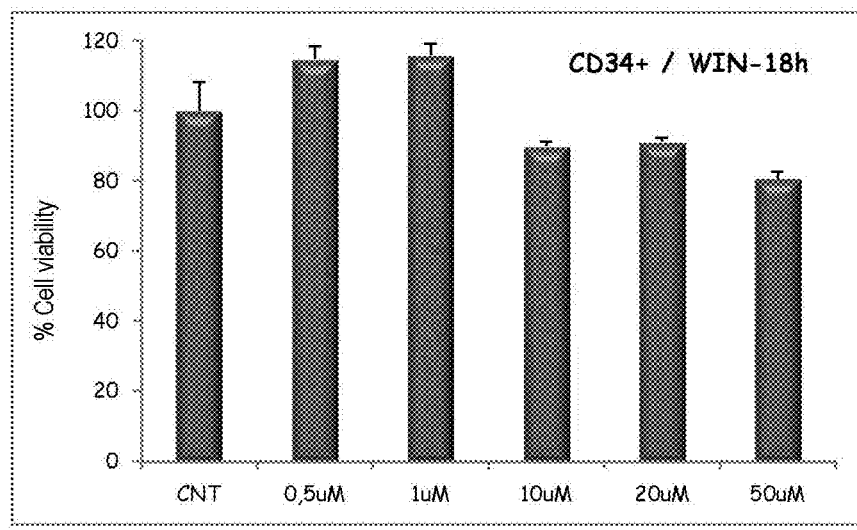
FIG. 6: CD34+ cells, hematopoietic progenitors (A) were isolated from peripheral blood, and the cytotoxicity of WIN was determined by the MTT assay after 18 h of incubation. The primary cultures of bone marrow were incubated for 18 h with the cannabinoid at the same concentrations used in the preceding assays. The population of polymorphonuclear cells (B) was identified with anti-CD64, and it was observed that the cell viability of this population determined by means of labeling with 7AAD was not affected by the cannabinoid. After ex vivo treatment for 18 h with the cannabinoid agent, it can be seen that the cell viability of the population of lymphocytes (C) in the primary culture of the bone marrow, CD45+, is affected at the concentration of 50 uM, dropping by 40%. However, the population of plasma cells (D) is drastically reduced after incubation at doses of 20 uM and 50 uM, the cell viability of this population being reduced in the latter case by more than 80%.
Figure 6B:
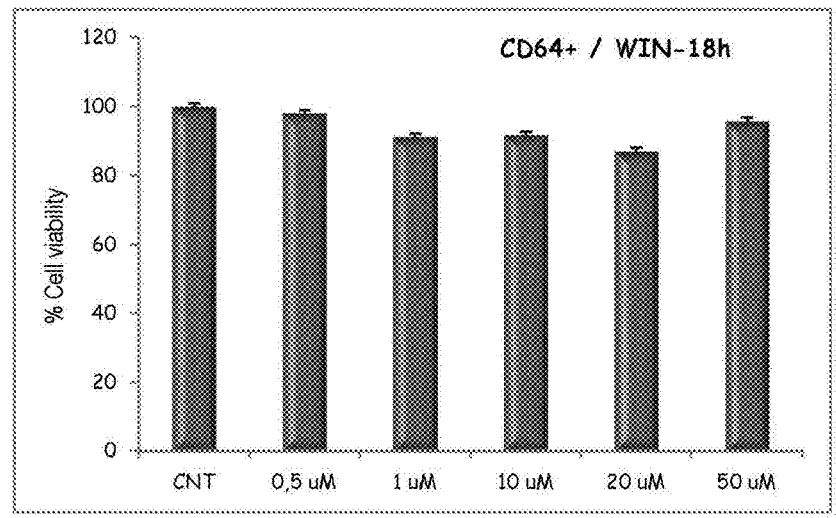
Figure 6C:
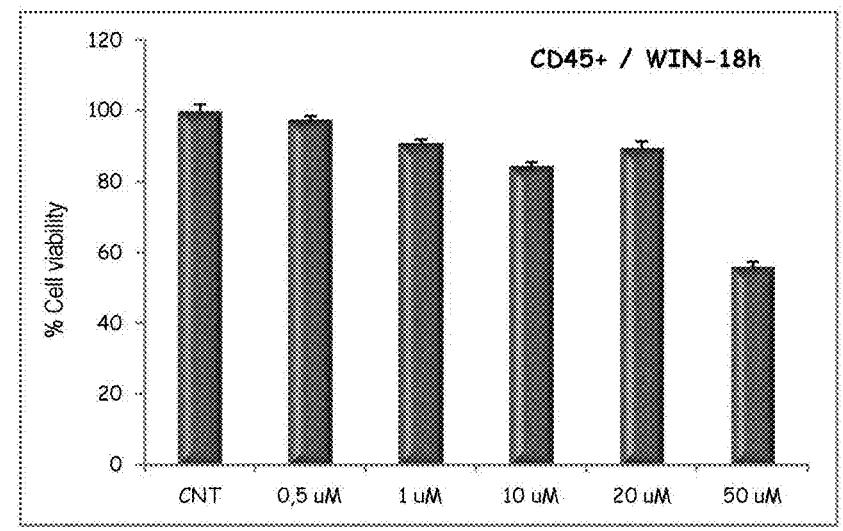
Figure 6D:
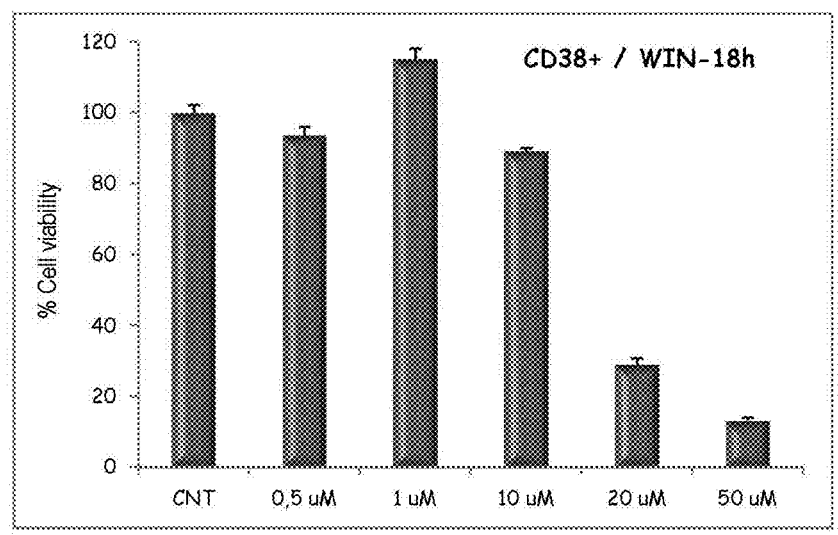

In this sense, in order to carry out these assays the authors incubated the myeloma cell line MM1.S at different concentrations with the cannabinoid agent WIN 55-212,2 for 48 and 96 hours, and cell viability was determined by means of MTT metabolization. Mean proliferation values of untreated control cell cultures were taken as 100%. The data corresponds to the means+/−the standard deviation of the triplicates of each of the 4 assays performed. As can be seen in FIGS. 4 and 5, cell viability noticeably dropped after concentrations greater than 1 uM when MM1.S cells were incubated for 48 hours. Cell viability also drops after 96 hours of exposure to the drug at the same concentrations. It can be deduced from this data that cell line MM1.S is more sensitive to WIN 55,212-2 than cell line U266. This data allows assuring the potentiality of compound WIN 55,212-2 as an effective therapy for the treatment of multiple myeloma and of related diseases.

Finally, the authors of the present invention evaluated the toxicity of cannabinoid agent WIN 55,212-2, which was determined in terms of cell viability by means of two types of assays, one based on the drop in 3(4,5dimethyl-2-thiazoyl)-2,5-diphenyltetrazolic bromide (MTT), and another one based on the interaction of 7AAD. Primary cultures of mononuclear cells obtained from peripheral blood from healthy donors (CD34+ hematopoietic progenitors) and from bone marrow of patients suffering multiple myeloma (CD64+, granulocytes (B), CD45+, lymphocytes (C) and CD38+, plasma cells (D)) were used.

CD34+ hematopoietic progenitor cells were isolated from apheresis of healthy donors by immunomagnetic methods. To that end, the cells were incubated for 30 min at 4° C. with magnetic microspheres bound to the anti-CD34 antibody. Subsequently the cells were selected by means of an immunomagnetic separator, and subsequently cultured in multiwell plates at a cell density of a million cells per milliliter of supplemented RPMI medium plus 20% fetal bovine serum (FBS).

The plasma cells, granulocytes and lymphocytes were obtained from bone marrow samples from patients with multiple myeloma after hypotonic lysis with ammonium chloride (0.16 M in 0.17 M Tris, pH 7.6) for 10 min at room temperature, for the purpose of removing the erythrocyte cell population. The cell suspension resulting from lysis, which only contains mononuclear cells, was seeded in multiwell plates at the same cell density as the progenitor cells using supplemented RPMI medium plus 20% fetal bovine serum.

The primary cultures were incubated in the presence and absence of the cannabinoid agent WIN 55,212-2 at different concentrations. The range of concentrations assayed with agent WIN 55,212-2 was 0.5-50 micromol. The incubation times of the primary cultures in the presence or absence of the cannabinoid agent were 12 or 18 hours.

As can clearly be seen in FIGS. 6A-6D, cell viability was not affected in the populations of hematopoietic progenitors (A) and granulocytes (B). In the population of lymphocytes (C), loss of viability was only detected at the highest dose. However, WIN produces a drastic drop in the cell viability of plasma cells (D) when they are treated at doses greater than 10 uM.

These results demonstrate that the use of agonist compounds of CB1 and/or CB2 cannabinoid receptors, particularly WIN 55,212-2, show not only cytoxicity against established myeloma cell lines but also that these compounds have a low toxicity profile, which paves the way for the use thereof as a promising therapy against multiple myeloma and related diseases. Therefore, an CB1 receptor agonist agent, a CB2 receptor agonist, or a mixed agonist can be used in the preparation of a medicinal product for the prevention and/or treatment of a monoclonal gammopathy, particularly for the prevention and/or treatment of multiple myeloma, plasma cell leukemia, Waldenström macroglobulinemia and amyloidosis.

Therefore, a first aspect of the invention relates to the use of an agent of a cannabinoid nature in the preparation of a medicinal product for the prevention and/or treatment of a monoclonal gammopathy. In a preferred embodiment, the monoclonal gammopathy is selected from the list consisting of: multiple myeloma, plasma cell leukemia, Waldenström macroglobulinemia and amyloidosis.

In another preferred embodiment, the cannabinoid agent is selected from natural cannabinoid agents or synthetic cannabinoid agents. In another preferred embodiment, the agent of a cannabinoid nature is selected from a CB1 receptor agonist, a CB2 receptor agonist, or a mixed agonist.

In another more preferred embodiment, the synthetic cannabinoid agent is selected from the list consisting of: HU-308; L-759, 633; PRS 21 1,375; AM-1241; 2-(3-methylcylohexyl)-5-(1,1,-'-dimethylheptyl)-resorcinol isomers (0 to 1,797 and 0-1798); 2-(3R-methylcylohexyl)-5-(1,-dimethylheptyl)-resorcinol (0-1826); bicyclic hydroxyl resorcinol derivatives; 1-{4-(1,1-Dimethyl-heptyl)-2,6-dimethoxyphenyl}-3-methyl-cyclohexanol (0 to 2137, 0-1966, 0-1967); JWH-015; L-759, 656; GW-842, 166X; GP-1 a; THC; HU-210; L-759, 656; WIN 55,212-2; CP 55940; CRA-13 (SAB-378); JWH-018 (AM-678) CP 50,556-1 (levonantradol), cannabidiol+THC, or any combinations thereof.

More preferably, the cannabinoid agent is WIN 55,212-2. WIN 55,212-2 is understood in this specification as a compound having IUPAC (International Union of Pure and Applied Chemistry) chemical formula (R)-(+)-[2,3-Dihydro-5-methyl-3-(4-morpholinylmethyl)pyrrolo[1,2,3-de]-1,4 benzoxazin-6-yl]-1-naphtalenylmethanone, CAS number 131543-23-2, and formula (I):

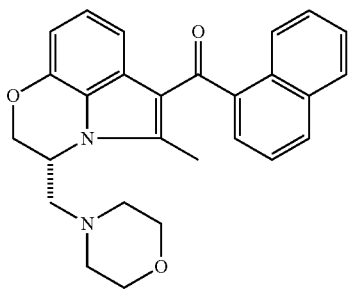

Formula (I)

or any pharmaceutically acceptable salts, solvates and prodrugs of said compound.

The term "pharmaceutically acceptable salts and solvates" refers to any pharmaceutically acceptable salt, ester, solvate, or any other compound which, when administered, is capable of providing (directly or indirectly) a compound such as the one described herein. Nevertheless, it will be observed that pharmaceutically unacceptable salts also fall within the scope of the invention, since such salts can be useful for the preparation of pharmaceutically acceptable salts. The preparation of salts, prodrugs and derivatives can be carried out by means of methods known in the state of the art.

For example, the pharmaceutically acceptable salts of the compounds provided herein are synthesized from the compound of the invention by means of conventional chemical methods. In general, such salts are prepared, for example, by reacting the acid or free base forms of these compounds with a stoichiometric amount of the base or the acid suitable in water or in a solvent organic or in a mixture of both. In general, non-aqueous media such as ether, ethyl acetate, ethanol, isopropanol or acetonitrile are preferred. Examples of the acid addition salts include addition salts of mineral acids such as, for example, hydrochloride, hydrobromide, hydroiodide, sulfate, nitrate, phosphate, and addition salts of organic acids such as, for example, acetate, maleate, fumarate, citrate, oxalate, succinate, tartrate, malate, mandelate, methanesulfonate and p-toluenesulfonate.

Examples of alkali addition salts include inorganic salts such as, for example, sodium, potassium, calcium, ammonium, magnesium, aluminum and lithium, and organic alkali salts such as, for example, ethylenediamine, ethanolamine, N,Ndialkylenethanolamine, glucamine and basic amino acid salts.

Particularly preferred derivatives or prodrugs are those which increase the bioavailability of the compounds of the invention when these compounds are administered to the subject (for example, those which allow an orally administered compound to be absorbed more quickly in the blood) or which improve the delivery of the compound to a biological compartment (for example, the brain or lymphatic system) with respect to the initial compound.

In another preferred embodiment, the cannabinoid agent is natural and is selected from the list consisting of: cannabigerol (CBG) type agents, cannabichromene (CBC) type agents, cannabidiol (CBD) type agents, cannabinodiol (CBND) type agents, tetrahydrocannabinol (THC) type agents, cannabinol (CBN) type agents, cannabitriol (CBT) agents, cannabielsoin (CBE) agents, isocannabinoid agents, cannabicyclol (CBL) type agents, cannabicitran (CBT) type agents, cannabichromanone (CBCN) type agents, or any combinations thereof.

In another more preferred embodiment, the natural cannabinoid agent is a cannabigerol (CBG) type agent, which is selected from the list consisting of: cannabigerol (E)-CBG-$C_5$; cannabigerol monomethyl ether (E)-CBGM-$C_5$ A; cannabinerolic acid A (2)-CBGA-$C_5$ A; cannabigerovarin (E)-CBGV-$C_3$; cannabigerolic acid A (E)-CBGA-$C_5$ A; cannabigerolic acid A monomethyl ether (E)-CBGAM-$C_5$ A; cannabigerovarinic acid A (E)-CBGVA-$C_3$ A, or any combinations thereof.

In another more preferred embodiment, the natural cannabinoid agent is a cannabichromene (CBC) type agent, which is selected from the list consisting of: (±)-cannabichromene CBC-$C_5$; (±)-cannabichromenic acid A CBCA-$C_5$ A; (±)-cannabichromevarin CBCV-$C_3$; (±)-cannabichromevarinic acid A CBCVA-$C_3$A, or any combinations thereof.

In another more preferred embodiment, the natural cannabinoid agent is a cannabinodiol (CBND) type agent, which is selected from the list consisting of: (−)-cannabidiol CBD-$C_5$; cannabidiol monomethyl ether CBDM-$C_5$; cannabidiol-$C_4$CBD-$C_4$; (−)-cannabidivarin CBDV-$C_3$; cannabidiorcol CBD-$C_1$; cannabidiolic acid CBDA-$C_5$; cannabidivarinic acid CBDVA-$C_3$, or any combinations thereof.

In another more preferred embodiment, the natural cannabinoid agent is a cannabinodiol (CBND) type agent, which is selected from the list consisting of: cannabinodiol CBND-$C_5$; cannabinodivarin CBND-$C_3$, or any combinations thereof.

In another more preferred embodiment, the natural cannabinoid agent is a tetrahydrocannabinol (THC) type agent, which is selected from the list consisting of: $\Delta^9$-Tetrahydrocannabinol $\Delta^9$-THC-$C_5$; $\Delta^9$Tetrahydrocannabinol-$C_4\Delta^9$-THC-$C_4$; $\Delta^9$-Tetrahydrocannabivarin $\Delta^9$-THCV-$C_3$; $\Delta^9$-Tetrahydrocannabiorcol $\Delta^9$-THCO-$C_1$; $\Delta^9$-Tetrahydrocannabinolic acid A $\Delta^9$-THCA-$C_5$A; $\Delta^9$-tetrahydrocannabinolic acid B $\Delta^9$-THCA-$C_5$ B; $\Delta^9$-tetrahydrocannabinolic acid-$C_4$ A and/or B; $\Delta^9$-THCA-$C_4$ A and/or B; $\Delta^9$-tetrahydrocannabivarinic acid A $\Delta^9$-THCVA-$C_3$A; $\Delta^9$-tetrahydrocannabiorcolic acid A and/or B $\Delta^9$-THCOA-d A and/or B; (−)-$\Delta^8$-trans (6aR,10aR)-$\Delta^8$-Tetrahydrocannabinol $\Delta^8$-THC-$C_5$; (−)-$\Delta^8$-trans-(6aR,10aR)-tetrahydrocannabinolic acid A $\Delta^8$-THCA-$C_5$A; (−)-(6aS,10aR)-$\Delta^9$-tetrahydrocannabinol (−)-cis-$\Delta^9$-THC-$C_5$, or any combinations thereof.

In another more preferred embodiment, the natural cannabinoid agent is a cannabinol (CBN) type agent, which is selected from the list consisting of: cannabinol CBN—$C_5$; cannabinol-$C_4$CBN—$C_4$; cannabivarin CBN—$C_3$; cannabinol-$C_2$CBN—$C_2$; cannabiorcol CBN—$C_1$; cannabinolic acid A CBNA-$C_5$A; cannabinol methyl ether CBNM-$C_5$, or any combinations thereof.

In another more preferred embodiment, the natural cannabinoid agent is a cannabitriol (CBT) type agent, which is selected from the list consisting of: (−)-(9R,10R)-trans-cannabitriol (−)-trans-CBT-$C_5$; (+) (9S,10S)-Cannabitriol (+)-trans-CBT-$C_5$; (±)-(9R,10S/9S,10R)-Cannabitriol (±)-cis-CBT-$C_5$; (−)-(9R,10R)-trans-10-O-Ethyl-cannabitriol (−)-trans-CBT-CEt-$C_5$; (±)-(9R,10R/9S,10S)-Cannabitriol-$C_3$(±)-trans-CBT-$C_3$; 8,9-Dihydroxy-$\Delta^{6a(10a)}$-tetrahydrocannabinol 8,9-Di-OH-CBT-$C_5$; cannabidiolic acid A cannabitriol ester CBDA-$C_5$ 9-OH-CBT-$C_5$ ester; (−)-(6aR,9S,10S,10aR)-9,10-Dihydroxy-hexahydrocannabinol, Cannabiripsol Cannabiripsol-$C_5$; (−)-6a,7,$10^a$ Trihydroxy-$\Delta^9$-tetrahydrocannabinol (−)-Cannabitetrol; 10-Oxo-$\Delta^{6a(10a)}$ tetrahydrocannabinol OTHC, or any combinations thereof.

In another more preferred embodiment, the natural cannabinoid agent is a cannabielsoin (CBE) type agent, which is selected from the list consisting of: (5aS,6S,9R,9aR)-Cannabielsoin CBE-$C_5$; (5aS,6S,9R,9aR)-$C_3$-Cannabielsoin CBE-$C_3$; (5aS,6S,9R,9aR)-cannabielsoic acid A CBEA-$C_5$ A; (5aS,6S,9R,9aR)-cannabielsoic acid B CBEA-$C_5$B; (5aS, 6S,9R,9aR)-$C_3$-cannabielsoic acid B CBEA-$C_3$ B; Cannabiglendol-$C_3$ OH-iso-HHCV—$C_3$; Dehydrocannabifuran DCBF—$C_5$; Cannabifuran CBF—$C_5$, or any combinations thereof.

In another more preferred embodiment, the natural cannabinoid agent is a isocannabinoid type agent, which is selected from the list consisting of: (−)-$\Delta^7$-trans-(1R,3R, 6R)-isotetrahydrocannabinol; (±)-$\Delta^7$-1,2-cis-(1R,3R,6S/1S, 3S,6R)-Isotetrahydro-cannabivarin; (−) $\Delta^7$-trans (1R,3R, 6R)-Isotetrahydrocannabivarin, or any combinations thereof.

In another more preferred embodiment, the natural cannabinoid agent is a cannabicyclol (CBL) type agent, which is selected from the list consisting of: (±)-(1aS,3aR,8bR, 8cR)-Cannabicyclol CBL-$C_5$; (±)-(1aS,3aR,8bR,8cR)-cannabicyclolic acid A CBLA-$C_5$ A; (±)-(1aS,3aR,8bR,8cR)-Cannabicyclovarin CBLV-$C_3$, or any combinations thereof.

In another more preferred embodiment, the natural cannabinoid agent is a Cannabicitran (CBL) type agent, which is selected from the list consisting of: Cannabicitran CBT-$C_5$, or any combinations thereof.

In another more preferred embodiment, the natural cannabinoid agent is an agent of the Cannabichromanone (CBCN) type, which is selected from the list consisting of: Cannabichromanone CBCN—$C_5$; Cannabichromanone-$C_3$; CBCN—$C_3$; Cannabicoumaronone CBCON—$C_5$, or any combinations thereof.

A second aspect of the invention relates to the use of a pharmaceutical composition comprising a cannabinoid agent described in the present invention for preparing a medicinal product for the prevention and/or treatment of a monoclonal gammopathy. More preferably, the monoclonal gammopathy is selected from the list consisting of: multiple myeloma, plasma cell leukemia, Waldenström macroglobulinemia and amyloidosis.

More preferably, the composition furthermore comprises another active ingredient. Even more preferably the active ingredient is selected from Velcade, Melfalan, Prednisone, Revlimd, Dextamethasone, Thalidomide, Doxyrubicin, Bortezomid, Mozobil, granulocyte colony-stimulating factor, pomailidomide, carfizomid, or any combinations thereof. Even more preferably the pharmaceutical composition comprises a pharmaceutically acceptable carrier.

Another aspect of the invention relates to the use of a combined preparation comprising a cannabinoid agent of the invention and another active ingredient in the preparation of a medicinal product for the simultaneous or sequential combined administration thereof for the treatment of a monoclonal gammopathy. More preferably, the monoclonal gammopathy is selected from multiple myeloma, plasma cell leukemia, Waldenström macroglobulinemia, amyloidosis, or any combinations thereof. In an even more preferred embodiment, the monoclonal gammopathy is multiple myeloma. Even more preferably the active ingredient is selected from Velcade, Melfalan, Prednisone, Revlimd, Dextamethasone, Thalidomide, Doxyrubicin, Bortezomid, Mozobil, granulocyte colony-stimulating factor, pomailidomide, carfizomid, or any combinations thereof.

In another preferred embodiment, the combined preparation of the invention furthermore comprises a pharmaceutically acceptable carrier. In another preferred embodiment, the combined preparation of the invention furthermore comprises another active ingredient.

As it is used in the context of this specification, the term "treatment" means the administration of a compound according to the invention to alleviate or eliminate the aforementioned pathology or to reduce or eliminate one or more symptoms associated with said pathology.

The term "treatment" also covers alleviating or eliminating the physiological sequelae of the disease.

As it is used herein, the term "prevention" refers to the capacity of a compound of the invention to prevent, minimize or hinder the onset or the development of a disease or state before onset.

The compounds of the invention can be in crystalline form as free compounds or solvates, and both forms are intended to be within the scope of the present invention. Solvation methods are generally known in the art. Suitable solvates are pharmaceutically acceptable solvates. In a particular embodiment, the solvate is a hydrate.

The compounds of the invention or the salts or solvates thereof are preferably in a pharmaceutically acceptable form or in a substantially pure form. Pharmaceutically acceptable form is understood, inter alia, as having a pharmaceutically acceptable level of purity, excluding normal pharmaceutical additives, such as diluents and excipients, and without including any material considered toxic at normal dosage levels. The levels of purity for the compound of the invention are preferably above 50%, more preferably above 70%, and even more preferably above 90%. In a preferred embodiment, it is above 95% of the compound of the invention, or of the salts, solvates or prodrugs thereof.

The compounds of the present invention can include enantiomers depending on the presence of chiral centers or isomers depending on the presence of multiple bonds (for example, Z, E). Individual isomers, enantiomers or diastereomers and mixtures thereof are within the scope of the present invention. When a compound with explicit stereochemistry is drawn, the intention is to depict the racemic structure with the relative stereochemistry, as well as the enantiomers in different degrees of purity. In any case, the enantiomers and the diastereoisomers of the compounds depicted with a particular stereochemistry are also part of the compounds of the invention.

Said compositions can have one or more cannabinoid agents. Said cannabinoid agents could be combined at identical or different proportions, and they could be part of the same formulation or be formulated in different formulations for the sequential, combined or simultaneous administration thereof.

In another preferred embodiment, the composition of the invention furthermore comprises a pharmaceutically acceptable carrier. In another preferred embodiment, the composition of the invention furthermore comprises another active ingredient.

The pharmaceutical compositions of the invention are administered by topical, transdermal, oral, nasal, intramuscular, intravenous, intraperitoneal, subcutaneous, enteral or parenteral administration. Illustrative examples of topical or transdermal administration include, but are not limited to, iontophoresis, sonophoresis, electroporation, mechanical pressure, osmotic pressure gradient, occlusive cure, microinjections, needle-free injections by means of pressure, microelectric patches and any combination thereof. Illustrative examples of pharmaceutical dosage forms by oral administration include tablets, capsules, granules, solutions, suspensions, etc., and can contain conventional excipients, such as binders, diluents, disintegrants, lubricants, humectants, etc., and can be prepared by conventional methods. The pharmaceutical compositions also can be adapted for the parenteral administration thereof in the form of, for example, sterile lyophilized solutions, suspensions or products in the suitable dosage form; in this case, said pharmaceutical compositions will include suitable excipients, such as buffers, surfactants, etc. In any case, the excipients will be chosen depending on the selected pharmaceutical dosage form. A review of the different pharmaceutical dosage forms of drugs and of the preparation thereof can be found in the book "Tratado de Farmacia Galénica," by C. Faulí Trillo, 10th Edition, 1993, Luzán 5, S. A. de Ediciones.

As it is used herein, the term "active ingredient," "active substance," "pharmaceutically active substance," or "pharmaceutically active ingredient" means any component that potentially provides pharmacological activity or another different effect in the diagnosis, cure, mitigation, treatment, or prevention of a disease, or that affects structure or function of the body of humans or other animals. The term includes those components that promote a chemical change in the preparation of the drug and are present therein in a modified form envisaged for providing the specific activity or effect.

The compositions of the present invention as well as the combined preparation can be formulated for the administration thereof to an animal, and more preferably to a mammal, including humans, in a variety of forms known in the state of the art. Therefore, it can be, without limitation, in a sterile aqueous solution or in biological fluids such as serum. The aqueous solutions can be buffered or not buffered and have additional active or inactive components. The additional components include salts for modulating the ionic force, preservatives including, but not limited to, antimicrobial agents, antioxidant agents, chelating agents and the like, and nutrients including glucose, dextrose, vitamins and minerals. Alternatively, the compositions can be prepared for the administration thereof in solid form. The compositions can be combined with several inert excipients or carriers, including but not limited to, binders such as microcrystalline cellulose, tragacanth gum, or gelatin; excipients such as starch or lactose; dispersing agents such as alginic acid or corn starch; lubricants such as magnesium stearate; glidants such as colloidal silicon dioxide; sweetening agents such as sucrose or saccharine; or flavoring agents such as mint or methyl salicylate.

As it is used in this specification, the term "medicinal product" refers to any substance used for the prevention, diagnosis, alleviation, treatment or curing of diseases in humans and animals. In the context of the present invention, the disease is a disease presenting with uncontrolled proliferation of plasma cells in bone marrow; it is preferably a multiple myeloma.

Such combined preparations or compositions and/or the formulations thereof can be administered to an animal, including a mammal, and therefore to humans, in a variety of forms, including, but not limited to, intraperitoneal, intravenous, intramuscular, subcutaneous, intrathecal, intraventricular, oral, enteral, parenteral, intranasal or dermal.

The dosage for obtaining a therapeutically effective amount depends on a range of factors, such as, for example, the age, weight, sex, tolerance of the mammal. In the sense used in this description, the expression "therapeutically effective amount" refers to the amount of agent or cannabinoid agents producing the desired effect, and it will generally be determined, between other causes, by the characteristics of said prodrugs, derivatives or analogues and the therapeutic effect to be achieved. The "pharmaceutically acceptable carriers" and "adjuvants" that can be used in said compositions are those carriers known by persons skilled in the art.

Another aspect of the invention relates to the use of a dosage form comprising a cannabinoid agent described in the preceding aspects of the invention, in the preparation of a medicinal product for the prevention and/or treatment a monoclonal gammopathy.

In a preferred embodiment of this aspect of the invention, the monoclonal gammopathy is multiple myeloma.

In another preferred embodiment, the combined preparation of the invention furthermore comprises a pharmaceutically acceptable carrier. In another preferred embodiment, the combined preparation of the invention furthermore comprises another active ingredient.

It must be stressed that the term "combined preparation" or also "juxtaposition" in this specification means that the components of the combined preparation do not have to be present as a combination, for example in a composition, to be available for the separate or sequential application thereof. Therefore, the expression "juxtaposed" means that it is not necessarily a real combination in view of the physical separation of the components.

Throughout the description and claims the word "comprises" and variants thereof do not seek to exclude other technical features, additives, components or steps. For the persons skilled in the art, other objects, advantages and features of the invention will be understood in part from the description and in part from putting the invention into practice. The following examples and drawings are provided by way of illustration and does not seek to be limiting of the present invention.

EXAMPLES

Example 1

Materials and Methods

MTT Assay Viability Analysis

The method for the determination of cell viability by means of the MTT assay is based on the capacity that viable cells have of metabolizing 3-(4,5-dimethylthiazol-2-yl)-2,5-diphenyltetrazol (MTT) bromide. The metabolic reduction of MTT due to the action of the mitochondrial enzyme, succinate dehydrogenase, gives rise to the insoluble and colored form called formazan, which can be quantified by means of spectrocolorimetry. The amount of living cells is proportional to the optical density resulting.

After incubation with cannabinoids, 10 microliters of MTT were added to each well and were incubated 2-4 hours in the same conditions. The reaction is subsequently stopped, the crystallized formazan is solubilized and optical density was determined at 450 nm in a plate spectrophotometer. All the assays were performed in triplicate.

Viability Analysis by Flow Cytometry

For the viability analysis by means of flow cytometry, the cells were treated with suitably labeled monoclonal antibodies for the identification of each of the cell types used. Once labeled; the cells were exposed for 15 min to 7AAD (7-actinomycin D) to evaluate cell viability; the reading was performed in the cytometer and analyzed with the computer program adapted for the cytometer. At least 100,000 events were acquired, and the mean fluorescence intensity was obtained.

Statistical Analysis

The data obtained in the plate spectrophotometer and in the cytometer were analyzed quantitatively by comparison with the Student's t-test using the statistical program SPSS. The results were considered statistically significant when p<0.05.

Example 2

Cytoxicity of Cannabinoid Compound WIN 55,212-2 in Myeloma Cell Line U266

To determine the effect of cannabinoid compound WIN 55,212-2, myeloma cell line U266 was incubated for a period of 48 and 96 hours with increasing concentrations of WIN 55,212-2 between 0.5 and 50 uM; cell viability was determined by means of MTT metabolization. The MTT assay is based on the capacity of the mitochondrial enzyme, succinate dehydrogenase, of viable cells to transform tetrazolium salt MTT into a blue-colored product, formazan MTT, which is proportional to the number of living cells present. Mean proliferation values of untreated control cell cultures were taken as 100%.

As can be seen in FIG. 1, concentrations between 10 and 20 uM of the compound WIN 55,212-2 were capable of inhibiting cell viability by about 40%, and concentrations of 50 uM produced cell viability inhibition of about 60%. Additionally, as reflected in FIG. 2, longer incubation periods, specifically of 96 hours, produced cell viability inhibition of about 80% at concentrations of 50 uM.

These same assays were repeated, incubating myeloma cell line U266 for a period of 48 hours with increasing concentrations of WIN 55,212-2 between 0.5 and 50 uM. Nevertheless, cell viability was determined by means of flow cytometry instead of by means of MTT metabolization. The results are illustrated in FIG. 3 and as can be seen, such results are very similar to those already described above in FIGS. 1 and 2.

Example 3

Cytoxicity of Cannabinoid Compound WIN 55,212-2 in Multiple Myeloma Cell Line MM1.S For the purpose of verifying the results described in Example 1, the authors of the present invention analyzed the capacity of the compound WIN 55,212-2 to inhibit viability of a second myeloma cell line, in this case multiple myeloma cell line MM1.S. The results of these experiments have been faithfully reflected in FIGS. 4 and 5.

In this sense, in order to carry out these assays the authors incubated myeloma cell line MM1.S at different concentrations with the cannabinoid agent WIN 55-212,2 for 48 and 96 hours, and cell viability was determined by means of MTT metabolization. Mean proliferation values of untreated control cell cultures were taken as 100%. The data corresponds to the means +/− the standard deviation of the triplicates of each of the 4 assays performed. As can be seen in FIGS. 4 and 5, cell viability noticeably dropped after concentrations greater than 1 uM when MM1.S cells were incubated for 48 hours. Cell viability also drops after 96 hours of exposure to the drug ay the same concentrations. It can be deduced from this data that cell line MM1.S is more sensitive to WIN 55,212-2 than cell line U266. This data allows asserting the potential of compound WIN 55,212-2 as effective therapy for the treatment of multiple myeloma and of related diseases.

Example 4

Cytoxicity of Cannabinoid Compound WIN 55,212-2 on Mononuclear Cells Obtained from Peripheral Blood of Healthy Donors (CD34+ Hematopoietic Progenitors) and from Bone Marrow of Patients Suffering Multiple Myeloma (CD64+, Granulocytes (B), CD45+, Lymphocytes (C) v CD38+, Plasma Cells (D))

The authors of the present invention evaluated the toxicity of cannabinoid agent WIN 55,212-2, which was determined in terms of cell viability by means of two types of assays, one based on the drop in 3(4,5dimethyl-2-thiazoyl)-2,5-diphenyltetrazolic (MTT) bromide, and another one based on the interaction of the 7AAD. Primary cultures of mononuclear cells obtained from peripheral blood of healthy donors (CD34+ hematopoietic progenitors) and from bone marrow of patients suffering multiple myeloma (CD64+, granulocytes (B), CD45+, lymphocytes (C) and CD38+, plasma cells (D)) were used.

CD34+ hematopoietic progenitor cells were isolated from healthy donors using apheresis by immunomagnetic methods. To that end, the cells were incubated for 30 min at 4° C. with microspheres magnetic bound to the anti-CD34 antibody. Subsequently the cells were selected by means of an immunomagnetic separator and then cultured in multi-well plates at a cell density of million cells per milliliter of supplemented RPMI medium plus 20% fetal bovine serum (FBS).

The plasma cells, granulocytes and lymphocytes were obtained from bone marrow samples from patients with multiple myeloma after hypotonic lysis with ammonium chloride (0.16 M in 0.17 M Tris, pH 7.6) for 10 min at room temperature, for the purpose of removing the erythrocyte cell population. The cell suspension resulting from lysis, which only contains mononuclear cells, was seeded in multiwell plates at the same cell density as the progenitor cells using supplemented RPMI medium plus 20% fetal bovine serum.

The primary cultures were incubated in the presence and absence of cannabinoid agent WIN 55,212-2 at different concentrations. The range of concentrations assayed with the agent WIN 55,212-2 was 0.5-50 micromol. The incubation times of the primary cultures in the presence or absence of the cannabinoid agent were 12 or 18 hours.

As can clearly be seen in FIGS. 6A-6D, cell viability was not affected in the populations of hematopoietic progenitors (A) and granulocytes (B). In the population of lymphocytes (C) loss of viability was only detected at the highest dose. However, WIN produced a drastic a drop in cell viability of plasma cells (D) when treated a doses greater than 10 uM.

These results demonstrate that the use of CB1 and/or CB2 cannabinoid receptor agonist compounds, particularly WIN 55,212-2, show not only cytoxicity against established myeloma cell lines, but also these compounds have a low toxicity profile, which paves the way for the use thereof as a promising therapy against multiple myeloma and related diseases.

The invention claimed is:

1. A method for treating multiple myeloma in a subject in need thereof, the method comprising administering to said subject an effective amount of a cannabinoid agent, wherein the cannabinoid agent is WIN 55,212-2 having the following structure:

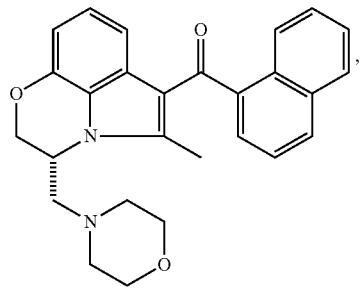 [SMILES: Cc1c(C(=O)c2cccc3ccccc23)c2cccc3c2n1[C@H](CN1CCOCC1)CO3]

or a salt or a solvate thereof, thereby treating said multiple myeloma in said subject.

2. A method for treating multiple myeloma in a subject in need thereof, the method comprising administering to said subject an effective amount of a pharmaceutical composition comprising a cannabinoid agent, wherein the cannabinoid agent is WIN 55,212-2 having the following structure:

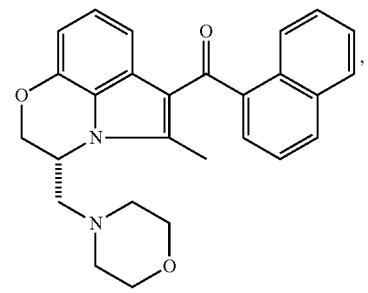 [SMILES: Cc1c(C(=O)c2cccc3ccccc23)c2cccc3c2n1[C@H](CN1CCOCC1)CO3]

or a salt or a solvate thereof, thereby treating said multiple myeloma in said subject.

3. The method according to claim 2, wherein the pharmaceutical composition comprises one or more pharmaceutically acceptable excipients.

4. A method for treating multiple myeloma in a subject in need thereof, the method comprising administering to said subject an effective amount of a cannabinoid agent, wherein the cannabinoid agent is WIN 55,212-2 having the following structure:

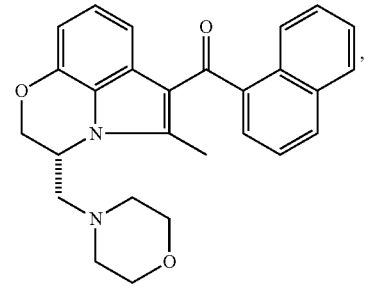 [SMILES: Cc1c(C(=O)c2cccc3ccccc23)c2cccc3c2n1[C@H](CN1CCOCC1)CO3]

or a salt or a solvate thereof, in combination with an active ingredient suitable for the treatment of multiple myeloma, thereby treating said multiple myeloma in said subject.

5. The method according to claim 4, wherein the active ingredient is selected from the group consisting of: Velcade, Melfalan, Prednisone, Revlimd, Dextamethasone, Thalidomide, Doxyrubicin, Bortezomid, Mozobil, granulocyte colony-stimulating factor, pomailidomide, carfizomid and any combination thereof.

6. The method according to claim 4, wherein the cannabinoid agent and the active ingredient are administered simultaneously.

7. The method according to claim 4, wherein the cannabinoid agent and the active ingredient are administered sequentially.

* * * * *